(12) United States Patent
Ellson et al.

(10) Patent No.: US 6,707,038 B2
(45) Date of Patent: Mar. 16, 2004

(54) METHOD AND SYSTEM USING ACOUSTIC EJECTION FOR SELECTIVE FLUID DEPOSITION ON A NONUNIFORM SAMPLE SURFACE

(75) Inventors: Richard N. Ellson, Palo Alto, CA (US); Mitchell W. Mutz, Palo Alto, CA (US); Richard Michael Caprioli, Brentwood, TN (US)

(73) Assignee: Picoliter Inc., Sunnyvale, CA (US)

( * ) Notice: Subject to any disclaimer, the term of this patent is extended or adjusted under 35 U.S.C. 154(b) by 0 days.

(21) Appl. No.: 10/157,755

(22) Filed: May 28, 2002

(65) Prior Publication Data

US 2002/0195558 A1 Dec. 26, 2002

Related U.S. Application Data

(63) Continuation-in-part of application No. 10/087,372, filed on Mar. 1, 2002, which is a continuation-in-part of application No. 10/066,546, filed on Jan. 30, 2002, which is a continuation-in-part of application No. 09/784,205, filed on Feb. 14, 2001, now Pat. No. 6,603,118.

(51) Int. Cl.[7] ............................. H01J 49/04; G01N 1/10; G01N 35/10
(52) U.S. Cl. ..................... 250/288; 436/180; 422/100; 422/63; 435/30; 73/864; 73/864.81
(58) Field of Search ..................... 250/288; 422/63, 422/100; 435/30; 436/180; 73/864

(56) References Cited

U.S. PATENT DOCUMENTS

| | | | |
|---|---|---|---|
| 4,308,547 A | 12/1981 | Lovelady et al. | |
| 4,751,529 A | 6/1988 | Elrod et al. | |
| 5,041,849 A | 8/1991 | Quate et al. | |
| 5,306,412 A | 4/1994 | Whitehouse et al. | |
| 5,520,715 A | 5/1996 | Oeftering | |
| 5,722,479 A | 3/1998 | Oeftering | |
| 5,798,779 A | 8/1998 | Nakayasu et al. | |
| 5,808,300 A * | 9/1998 | Caprioli | 250/288 |
| 5,808,636 A | 9/1998 | Stearns | |
| 5,877,580 A | 3/1999 | Swierkowski | |
| 6,291,820 B1 | 9/2001 | Hamza et al. | |
| 6,322,970 B1 | 11/2001 | Little et al. | |
| 6,327,030 B1 | 12/2001 | Ifju et al. | |
| 6,558,902 B1 | 5/2003 | Hillenkamp | |
| 2002/0037579 A1 | 3/2002 | Ellson et al. | |
| 2002/0061258 A1 | 5/2002 | Mutz et al. | |
| 2002/0064808 A1 | 5/2002 | Mutz et al. | |
| 2002/0064809 A1 | 5/2002 | Mutz et al. | |
| 2002/0090720 A1 | 7/2002 | Mutz et al. | |
| 2002/0094582 A1 * | 7/2002 | Williams et al. | 436/180 |

FOREIGN PATENT DOCUMENTS

EP    0434931 A2    7/1991

OTHER PUBLICATIONS

U.S. patent application Ser. No. 09/669,267, Ellson, filed Sep. 25, 2000.

(List continued on next page.)

*Primary Examiner*—Jack Berman
(74) *Attorney, Agent, or Firm*—Reed & Eberle LLP; Louis L. Wu (57) ABSTRACT

A method for selectively depositing analysis-enhancing fluid on a sample surface is disclosed. The method involves providing a sample having a surface that exhibits variations in a surface characteristic that corresponds to desirability for receiving an analysis-enhancing fluid. Once a site on the sample surface is selected according to the surface characteristic at the site, focused radiation, typically acoustic radiation, is applied in a manner effective to eject a droplet of the analysis-enhancing fluid from a reservoir. As a result, the droplet is deposited on the sample surface at the selected site. Optionally, the sample at the selected site is analyzed. Systems for selectively depositing analysis-enhancing fluids are also disclosed.

55 Claims, 3 Drawing Sheets

OTHER PUBLICATIONS

U.S. patent application Ser. No. 09/669,996, Ellson et al., filed Sep. 25, 2000.

U.S. patent application Ser. No. 09/669,997, Mutz et al., filed Sep. 25, 2000.

U.S. patent application Ser. No. 09/999,166, Mutz et al., filed Nov. 29, 2001.

Amemiya et al. (1979), *Proceedings of the 1997 IS&T's NIP 13: 1997 International Conference on Digital Printing Technologies*, pp. 698–702.

IUPAC–IUB Commission on Biochemical Nomenclature (CBN) (1970), "Abbreviations and Symbols for Nucleic Acids, Polynucleotides and Their Constituents," *Biochemistry* 9(20):4022–4025.

Karas et al. (1988), "Laser Desorption Ionization of Proteins with Molecular Masses Exceeding 10,000 Daltons," *Anal. Chem.* 60:2299–2301.

Steel et al. (2000), "The Flow–Thru Chip™: A Three–Dimensional Biochip Platform," *Microarray Biochip Technology*, Chapter 5, pp. 87–117, BioTechniques Books, Natick, MA.

Stoeckli et al. (2001), "Imaging Mass Spectrometry: A New Technology for the Analysis of Protein Expression in Mammalian Tissues," *Nature Medicine* 7(4):493–496.

\* cited by examiner

METHOD AND SYSTEM USING ACOUSTIC EJECTION FOR SELECTIVE FLUID DEPOSITION ON A NONUNIFORM SAMPLE SURFACE

CROSS-REFERENCE TO RELATED APPLICATIONS

This is a continuation-in-part of U.S. patent application Ser. No. 10/087372, filed Mar. 1, 2002, which is a continuation-in-part of U.S. patent application Ser. No. 10/066,546, filed Jan. 30, 2002, which is a continuation-in-part of U.S. patent application Ser. No. 09/784,705, filed Feb. 14, 2001 now U.S. Pat. No. 6,603,118, the disclosures of which are incorporated by reference herein.

TECHNICAL FIELD

This invention relates generally to methods and devices for selectively depositing fluids on a nonuniform sample surface according to variations in a surface characteristic. More particularly, the invention relates to the use of nozzleless acoustic ejection to deposit droplets of analysis-enhancing fluid on sample surface sites selected according to the surface characteristic at the sites. The invention is especially useful in enhancing the compositional analysis of the biological samples and in the mass spectrometric imaging of tissue surfaces.

BACKGROUND

Mass spectrometry is a well-established analytical technique in which sample molecules are ionized and the resulting ions are sorted by mass-to-charge ratio. As the requirements for surface analytical techniques have become more exacting, [advances in mass spectrometry have made it possible to obtain in-depth information regarding a wide variety of sample surface types. In the semiconductor industry, for example, secondary ion mass spectrometry has been used to determine the composition of a microscopic region of a wafer surface. In addition, in the biotechnology arena, surface-based mass spectrometry has been used to analyze single nucleotide polymorphisms in microarray formats. See, e.g., U.S. Pat. No. 6,322,970 to Little et al.

Matrix-Assisted Laser Desorption Ionization (MALDI) is an ionization technique often used for mass spectrometric analysis of large and/or labile biomolecules, such as nucleotidic and peptidic oligomers, polymers, and dendrimers, as well as for analysis of nonbiomolecular compounds, such as fullerenes. MALDI is considered a "soft" ionizing technique in which both positive and negative ions are produced. The technique involves depositing a small volume of sample fluid containing an analyte on a substrate comprised of a photon-absorbing matrix material selected to enhance desorption performance. See Karas et al. (1988), "Laser Desorption Ionization of Proteins with Molecular Masses Exceeding 10,000 Daltons," *Anal. Chem.*, 60:2299–2301. The matrix material is usually a crystalline organic acid that absorbs electromagnetic radiation near the wavelength of the laser. When co-crystallized with analyte, the matrix material assists in the ionization and desorption of analyte moieties. The sample fluid typically contains a solvent and the analyte. Once the solvent has been evaporated from the substrate, the analyte remains on the substrate at the location where the sample fluid has been deposited. Photons from a laser strike the substrate at the location of the analyte and, as a result, ions and neutral molecules are desorbed from the substrate. MALDI techniques are particularly useful in providing a means for efficiently analyzing a large number of samples. In addition, MALDI is especially useful in the analysis of minute amounts of sample that are provided over a small area of a substrate surface.

Surface Enhanced Laser Desorption Ionization (SELDI) is another example of a surface-based ionization technique that allows for high-throughput mass spectrometry. SELDI uses affinity capture reagents such as antibodies to collect samples from a complex mixture, which allows in situ purification of the analyte, followed by conventional MALDI analysis. Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, analytes can be partially purified on the chip and then quickly analyzed in the mass spectrometer. By providing different reactive moieties at different sites on a substrate surface, throughput may be increased.

Recently, mass spectrometry techniques involving laser desorption have been adapted for cellular analysis. U.S. Pat. No. 5,808,300 to Caprioli, for example, describes a method for imaging biological samples with MALDI mass spectrometry. This method allows users to measure the distribution of a specific element or small molecule within biological specimens such as tissue slices or individual cells. In particular, the method can be used for the specific analysis of peptides in whole cells, e.g., by obtaining signals for peptides and proteins directly from tissues and blots of tissues. In addition, the method has been used to desorb relatively large proteins from tissues and blots of tissues in the molecular weight range beyond about 80 kilodaltons. From such samples, hundreds of peptide and protein peaks can be recorded in the mass spectrum produced from a single laser-ablated site on the sample. When a laser ablates the surface of the sample at multiple sites and the mass spectrum from each site is saved separately, a data array is produced, which contains the relative intensity of any given mass at each site. An image of the sample surface can then be constructed for any given molecular weight, effectively representing a compositional map of the sample surface.

One important issue to successful MALDI profiling and imaging as described above is the application of a mass spectrometry matrix material to the tissue surface at each site of laser ablation. As described in Caprioli, the mass spectrometry matrix material may be applied as a continuous and uniform coating of less than about 50 micrometers in thickness. In order to apply the mass spectrometry matrix material in a controlled manner, carefully metered amounts of sample fluids should be accurately and precisely placed on a sample surface. Acoustic ejection is a technique that is well suited for depositing minute volumes of fluids on a surface because the technique allows for control over droplet volume and thus "spot" size on the surface, as well as control over the trajectory of ejected droplets and the precise location of the deposition sites on the surface. See, e.g., U.S. Patent Application Publication No. 20020037579 to Ellson et al. In particular, U.S. patent application Ser. No. 10/087372, entitled "Method and System Using Acoustic Ejection for Preparing and Analyzing a Cellular Sample Surface," filed Mar. 1, 2002, by inventors Ellson, Mutz, and Caprioli, describes the use of nozzleless acoustic ejection to deposit mass spectrometry matrix material at designated sites on a sample surface to form either a uniform matrix material layer or an array of individual sites. In some instances, different analysis-enhancing fluids may be applied to an analyte to optimize experimental parameters.

As with many types of samples, cellular samples are not typically uniform in composition, and the distribution of materials on the surface of such samples may vary. In addition, the sample surfaces may exhibit inhomogeneous morphologies. Since certain analysis-enhancing fluids are appropriate for use with certain analytes, there is a need to selectively deposit the analysis-enhancing fluid according to the surface characteristics of the cellular sample at that site. Acoustic ejection provides a means for carrying out such fluid deposition with unparalleled accuracy, precision, and efficiency.

SUMMARY OF THE INVENTION

Accordingly, one embodiment of the invention relates to a method for selectively depositing an analysis-enhancing fluid on a sample surface. The method involves providing a sample having a surface that exhibits variations in a specific characteristic, which corresponds to its desirability for receiving an analysis-enhancing fluid. Once a site on the sample surface has been selected according to the desired surface characteristic, focused radiation, typically acoustic radiation, is applied in a manner effective to eject a droplet of the analysis-enhancing fluid from a reservoir. As a result, the droplet is deposited on the sample surface at the selected site. In some instances, a plurality of sites is selected, and a droplet of the analysis-enhancing fluid is deposited onto each selected site. The sites may form a single contiguous region on the sample surface or a plurality of noncontiguous regions on the sample surface. Optionally, the sample at the selected sites is analyzed.

Although the invention may be practiced using any sample having a nonuniform surface, cellular samples are particularly well suited. Examples of suitable cellular samples include, for example, tissue samples, cell cultures, single cells, or a plurality of cells immobilized on a substrate surface. In addition, the invention is particularly suited for samples having a substantially planar surface.

The surface characteristic corresponding to desirability for receiving analysis-enhancing fluid is typically a compositional or a morphological characteristic that is optically and/or acoustically detectable. For example, when the sample surface is a tissue sample comprised of distinct fatty and lean regions, it may be desirable to deposit analysis-enhancing fluid on only the fatty region. In such a case, the sites for fluid deposition may be selected according to lipid and/or peptide content at the site. Thus, the analysis-enhancing fluid may be selected according to the type of analysis desired. In some instances, the analysis-enhancing fluid comprises a label moiety, such as one or more selected from the group consisting of a fluorescent moiety, a magnetic moiety, and a radioactive moiety. In addition or in the alternative, the analysis-enhancing fluid may contain a biomolecule, nucleotidic, peptidic, or otherwise. Often, an enzymatic biomolecule is provided to enhance breakdown of the corresponding substrate moiety on or near the sample surface.

In some instances, the sample may exhibit variations in a plurality of surface characteristics, wherein each characteristic corresponds to desirability for receiving a different analysis-enhancing fluid. In such a case, droplets of different analysis-enhancing fluids may be deposited on the sample surface at the corresponding selected sites. In addition, different analysis-enhancing fluids may be deposited on the sample surface at the same site.

The invention is particularly suited for mass spectrometric analysis. In order to carry out a surface-based mass spectrometry technique, mass spectrometry matrix material may be deposited on the sample surface, and energy is then applied to the deposited matrix material to cause release of sample molecules from the sample surface for analysis. Typically, the matrix material is a photoabsorbing matrix material, and a photon source such as a laser is used to ionize the sample.

Thus, the invention is also particularly suited for use with sample surface imaging. In some instances, a sample surface is imaged so as to map the variations in the surface characteristic, and one or more sites are selected on the sample surface using the results of surface imaging. Preferably, surface imaging results in the production of a digital image. Optionally, the imaging contrast of the variations in the surface characteristic is increased before the surface is imaged. This may involve, for example, staining the sample surface such that regions exhibiting the desired surface characteristic are more readily resolved by an imaging means.

In another embodiment, the invention provides a system for selectively depositing an analysis-enhancing fluid on a surface of a sample. The system includes a reservoir containing an analysis-enhancing fluid, an acoustic ejector comprising an acoustic radiation generator for generating acoustic radiation and a focusing means for focusing the acoustic radiation generated, and a means for positioning the acoustic ejector in acoustic coupling relationship to the reservoir. Also provided is a means for selecting at least one site on the sample surface for deposition of analysis-enhancing fluid thereon. Site selection is carried out according to a surface characteristic that corresponds to desirability for receiving the analysis-enhancing fluid. The system also includes a means for positioning the sample such that the selected site or sites are positioned in droplet-receiving relationship to the reservoir. The sample positioning means may be adapted to controllably position the sample such that when a plurality of sites on the sample surface is selected, the selected sites are successively placed in droplet-receiving relationship to the reservoir.

In some instances, the selecting means is comprised of a means for imaging of the sample surface so as to map the variations in the surface characteristic and a means for selecting at least one site on the sample surface using the results produced by the imaging means. The imaging means is typically adapted to produce a digital image and may, for example, employ a scanner or a camera. In other instances, an image of the sample surface that maps the variations in the surface characteristic is produced without an imaging means. For example, a low-resolution map of the compositional characteristics of the sample could be formed based on performing mass spectrometry of spots from a sparse grid of analysis-enhancing fluid deposited on the sample. In either case, the selecting means may select sites for analysis-enhancing fluid deposition when the surface characteristic is above a threshold level, below a threshold level and/or when the surface characteristic is within a predetermined range.

The inventive system may further include a means for analyzing the composition of the sample at the selected site. The analyzing means may include a mass spectrometer, an optical detector, a radiation detector, and/or a magnetic detector. A means for applying energy to the sample surface may be provided as well to effect release and ionization of sample molecules from the sample surface for analysis. For example, the energy applying means may include a laser and/or other means for bombarding the surface with photons.

In a further embodiment, the system may include a plurality of reservoirs, each containing a different analysis-enhancing fluid. In such a case, the site selecting means may select sites according to a surface characteristic that corresponds to desirability for receiving at least one of the analysis-enhancing fluids. In addition, the sample positioning means positions the sample such that the selected sites thereon are placed successively in droplet-receiving relationship to the reservoir containing the analysis-enhancing fluid that corresponds to the surface characteristic at the selected sites.

In still another embodiment, the selecting means represents an optional component of system, and the sample positioning means positions the sample such that at least one site on the sample surface exhibiting a surface characteristic that corresponds to desirability for receiving the analysis-enhancing fluid is placed in droplet-receiving relationship to the reservoir. This and other embodiments may be adapted to controllably position the sample such that when a plurality of sites on the sample surface exhibits the desired surface characteristic, the selected sites are successively placed in droplet-receiving relationship to the reservoir. In addition, the sample positioning means may include digital information that relates the location or locations for analysis-enhancing fluid deposition.

BRIEF DESCRIPTION OF THE DRAWINGS

The invention is described in detail below with reference to the following drawings, wherein like reference numerals indicate a corresponding structure throughout the several views. The figures illustrate an embodiment of the inventive method wherein a tissue sample is analyzed at selected sites through laser desorption-based mass spectrometry.

DETAILED DESCRIPTION OF THE INVENTION

Definitions and Overview

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include both singular and plural referents unless the context clearly dictates otherwise. Thus, for example, reference to "a reservoir" includes a plurality of reservoirs as well as a single reservoir, reference to "a fluid" includes a plurality of fluids as well as single fluid, reference to "a characteristic" includes a combination of characteristics as well as single characteristic, and the like.

In describing and claiming the present invention, the following terminology will be used in accordance with the definitions set forth below.

The terms "acoustic coupling" and "acoustically coupled" as used herein refer to a state wherein an object is placed in direct or indirect contact with another object so as to allow acoustic radiation to be transferred between the objects without substantial loss of acoustic energy. When two items are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The terms "acoustic radiation" and "acoustic energy" are used interchangeably herein and refers to the emission and propagation of energy in the form of sound waves. As with other waveforms, acoustic radiation may be focused using a focusing means, as discussed below.

The term "array" as used herein refers to a two-dimensional arrangement of features, such as an arrangement of reservoirs (e.g., wells in a well plate) or an arrangement of fluid droplets on a sample surface. Arrays are generally comprised of features regularly ordered in, for example, a rectilinear grid, parallel stripes, spirals, and the like; but nonordered arrays may be advantageously used as well. An array differs from a pattern in that patterns do not necessarily contain regular and ordered features.

The terms "biomolecule" and "biological molecule" are used interchangeably herein to refer to any organic molecule—whether naturally occurring, recombinantly produced, or chemically synthesized in whole or in part—that is, was, or can be a part of a living organism. The terms encompass, for example, nucleotides, amino acids, and monosaccharides, as well as oligomeric and polymeric species such as oligonucleotides and polynucleotides; peptidic molecules such as oligopeptides, polypeptides, and proteins; polysaccharides such as disaccharides, oligosaccharides, mucopolysaccharides, and peptidoglycans (peptido-polysaccharides); and the like. The term also encompasses ribosomes, enzyme cofactors, pharmacologically active agents, and the like.

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G), and uracil (U), but also protected forms thereof, e.g., wherein the base is protected with a protecting group such as acetyl, difluoroacetyl, trifluoroacetyl, isobutyryl, or benzoyl, and purine and pyrimidine analogs. Suitable analogs will be known to those skilled in the art and are described in the pertinent texts and literature. The terms "peptide," "peptidyl," and "peptidic" as used throughout the specification and claims are intended to include any structure comprised of two or more amino acids. For the most part, the peptides in the present arrays comprise about 5 to 10,000 amino acids, preferably about 5 to 1000 amino acids. The amino acids forming all or a part of a peptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Any of the amino acids in the peptidic molecules forming the present arrays may be replaced by a nonconventional amino acid. Additional information relating to the term "biomolecule" "nucleotide" and "peptide" can be found in U.S. Patent Application Publication No. 20020037579 to Ellson et al.

The term "fluid" as used herein refers to matter that is nonsolid or at least partially gaseous and/or liquid. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous. The term "analysis-enhancing fluid" refers to any fluid that may be required or desired for use in conjunction with an analytical technique. Typically, analysis-enhancing fluids are employed to increase yield of useful information during surface analysis.

The terms "focusing means" and "acoustic focusing means" refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and described, for example, in U.S. Pat. No. 5,798,779 to Nakayasu et al. and Amemiya et al. (1997) *Proceedings of the 1997 IS&T NIP13 International Conference on Digital Printing Technologies*, pp. 698–702.

The term "ion" is used in its conventional sense to refer to a charged atom or molecule, i.e., an atom or molecule that contains an unequal number of protons and electrons. Positive ions contain more protons than electrons, and negative ions contain more electrons than protons. Ordinarily, an ion of the present invention is singly charged, but may in certain instances have a multiple charge.

Accordingly, the term "ionization chamber" as used herein refers to a chamber in which ions are formed from samples—fluid or otherwise—that contain a sample molecule.

The term "moiety" as used herein refers to any particular composition of matter, e.g., a molecular fragment, an intact molecule (including a monomeric molecule, an oligomeric molecule, or a polymer), or a mixture of materials (for example, an alloy or a laminate).

The term "near," as used herein refers to the distance from the focal point of the focused acoustic radiation to the surface of the fluid from which a droplet is to be ejected and indicates that the distance should be such that the focused acoustic radiation directed into the fluid results in droplet ejection from the fluid surface so that one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

"Optional" or "optionally" means that the subsequently described circumstance may or may not occur, so that the description includes instances where the circumstance occurs and instances where it does not.

The term "radiation" is used in its ordinary sense and refers emission and propagation of energy in the form of a waveform disturbance traveling through a medium such that energy is transferred from one particle of the medium to another without causing any permanent displacement of the medium itself. Thus, radiation may refer, for example, to electromagnetic waveforms as well as acoustic vibrations.

The term "reservoir" as used herein refers to a receptacle or chamber for containing a fluid. Thus, a fluid in a reservoir necessarily has a free surface, i.e., a surface that allows a droplet to be ejected therefrom. A reservoir may also be a locus on a substrate surface within which a fluid is constrained or held. In some instances, a reservoir may represent a portion, e.g., a fluid-transporting feature of a microfluidic device.

The term "substantially" as in, for example, the phrase "substantially identical volume," refers to volumes that do not deviate by more than 10%, preferably not more than 5%, more preferably not more than 1%, and most preferably at most 0.1% from each other. Other uses of the term "substantially" involve an analogous definition.

The term "substrate" as used herein refers to any material having a surface onto which a sample—cellular or otherwise—may be placed and optionally immobilized. The substrate may be constructed in any of a number of forms, for example, wafers, slides, well plates, and membranes. In addition, the substrate may be porous or nonporous as may be required for deposition of a particular fluid. Suitable substrate materials include, but are not limited to, supports that are typically used for solid phase chemical synthesis, for example, polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, and divinylbenzene styrene-based polymers), agarose (e.g., Sepharose®), dextran (e.g., Sephadex®), cellulosic polymers and other polysaccharides, silica and silica-based materials, glass (particularly controlled pore glass (CPG) and functionalized glasses), ceramics, and such substrates treated with surface coatings, such as microporous polymers (particularly cellulosic polymers such as nitrocellulose), microporous metallic compounds (particularly microporous aluminum), antibody-binding proteins (available from Pierce Chemical Co., Rockford, Ill.), bisphenol A polycarbonate, or the like. Additional information relating to the term "substrate" can be found in U.S. Patent Application Publication No. 20020037579 to Ellson et al.

The term "surface modification" as used herein refers to the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying, or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

The term "tissue" as used herein refers to an aggregation of morphologically similar cells and associated intercellular matter acting together to perform one or more specific functions in a multicellular organism, e.g., a plant or an animal. When the tissue is from an animal, for example, the tissue may be muscle, nerve, epidermal, or connective.

In general, the invention relates to a method for selectively depositing an analysis-enhancing fluid on a nonuniform sample surface that exhibits variations in a surface characteristic, wherein the surface characteristic corresponds to desirability for receiving an analysis-enhancing fluid. The surface characteristic corresponding to desirability for receiving analysis-enhancing fluid is typically a compositional or a morphological characteristic. Once a site on the sample surface has been selected according to the surface characteristic at the site, focused radiation, typically acoustic radiation, is applied in a manner effective to eject a droplet of the analysis-enhancing fluid from a reservoir. In some instances, the sample may exhibit variations in a plurality of surface characteristics, wherein each characteristic corresponds to desirability for receiving a different analysis-enhancing fluid. In such a case, droplets of different analysis-enhancing fluids may be deposited on the sample surface at the corresponding selected sites.

Optionally, the sample at the selected site may be analyzed. Typical analytical techniques that benefit from the invention include, but are not limited to, mass spectrometry, structural analysis, and microscopy. In addition, the invention is also particularly suited for use with surface imaging techniques. In some instances, a sample surface is imaged so as to map the variations in the surface characteristic, and one or more sites are selected on the sample surface using the results of the surface imaging. Preferably, a surface imaging results in the production of a digital image. Further optionally, the imaging contrast of the variations in the surface characteristic is increased before the surface is imaged. This may involve, for example, staining the sample surface such that regions exhibiting the desired surface characteristic are more readily resolved by an imaging means.

Typically, though not necessarily, the inventive method may be carried out using a system for selectively depositing an analysis-enhancing fluid on a surface of a sample. The system includes a reservoir containing an analysis-enhancing fluid, an acoustic ejector comprising an acoustic radiation generator for generating acoustic radiation and a focusing means for focusing the acoustic radiation generated, and a means for positioning the acoustic ejector in acoustic coupling relationship to the reservoir. Also provided is a means for selecting at least one site on the sample surface for deposition of analysis-enhancing fluid thereon. Site selection is carried out according to a surface characteristic that corresponds to desirability for receiving the analysis-enhancing fluid. The system also includes a means for positioning the sample such that the selected site or sites are positioned in droplet-receiving relationship to the reservoir. The sample positioning means may be adapted to controllably position the sample such that when a plurality of sites on the sample surface is selected, the selected sites are successively placed in droplet-receiving relationship to the reservoir. Optionally, a means for analyzing the composition of the sample at the selected site may also be provided.

Figure 1:
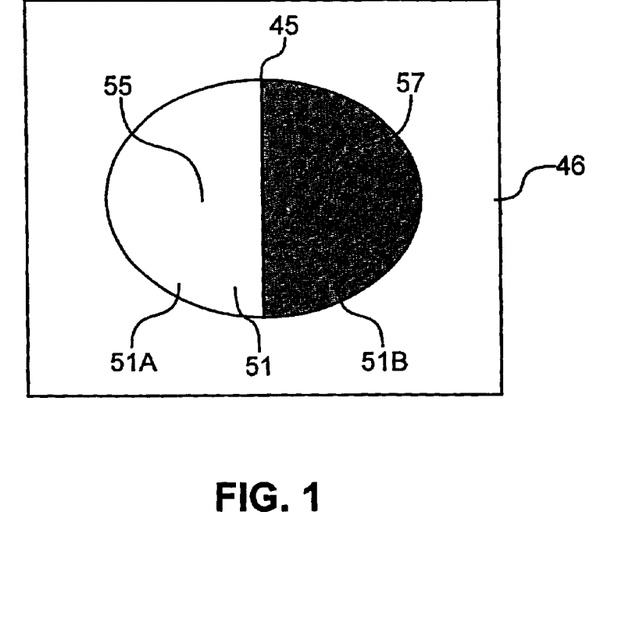
FIG. 1 schematically illustrates in top view a tissue sample on a substrate, wherein the tissue sample exhibits a nonuniform exposed surface.

FIGS. 1–5 illustrate an embodiment of the inventive method for selectively depositing and analyzing a cellular sample through mass spectrometry. As with all figures referenced herein, in which like parts are referenced by like numerals, FIGS. 1–5 are not to scale, and certain dimensions may be exaggerated for clarity of presentation. FIG. 1 illustrates an exemplary cellular sample 45 is placed on a substrate 46 for use with the invention. As depicted, the sample 45 is a tissue sample having a substantially planar and nonuniform surface 51. As shown, the surface 51 includes two distinct regions, the first region 51A depicted without shading, and the second region 51B, depicted with shading. Region 51A exhibits a first surface characteristic that corresponds to desirability for receiving a first analysis-enhancing fluid 14 (shown in FIGS. 3 and 4), and region 51B exhibits a second surface characteristic that corresponds to desirability for receiving a second analysis-enhancing fluid 16 (shown in FIGS. 3 and 4).

Figure 2:
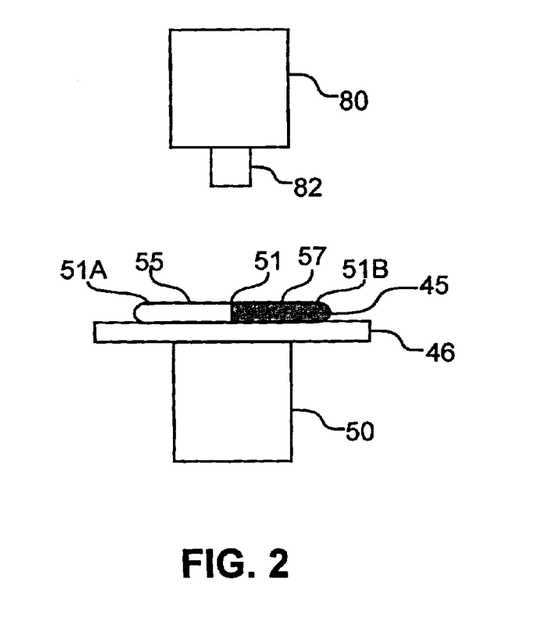
FIG. 2 schematically illustrates in side view the imaging of the exposed surface of the tissue sample.

In order to select sites on the sample according to desirability for receiving analysis-enhancing fluid, it may be necessary to image the sample surface. As shown in FIG. 2, a combination unit 80 is provided that serves as a selecting means and a controller. The combination unit includes an imaging means 82 adapted to produce a digital image of the sample surface 51. The digital image of the sample surface captured by the imaging means 82 is stored and optionally analyzed in the combination unit 80. As a result, one or more sites on the sample surface 51 may be selected according to the surface characteristics at the site or sites. This selection data, in turn, may be used in a system to selectively deposit fluids onto the sample surface at the sites. As depicted, once an image of the sample surface 51 is obtained, the combination unit, acting as a selecting means, will determine that site 55 in region 51A is desirable for receiving the first analysis-enhancing fluid 14 and site 57 in region 51B is desirable for receiving the second analysis-enhancing fluid 16.

Figure 3:
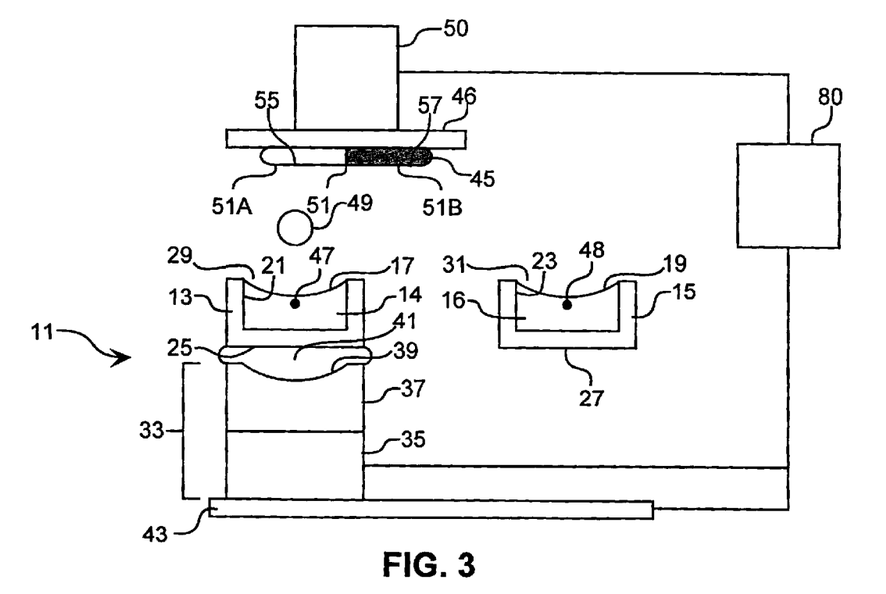
FIG. 3 schematically illustrates in side view the deposition of a first analysis-enhancing fluid on a surface of the tissue sample at a first site selected according to a first surface characteristic.
Figure 4:
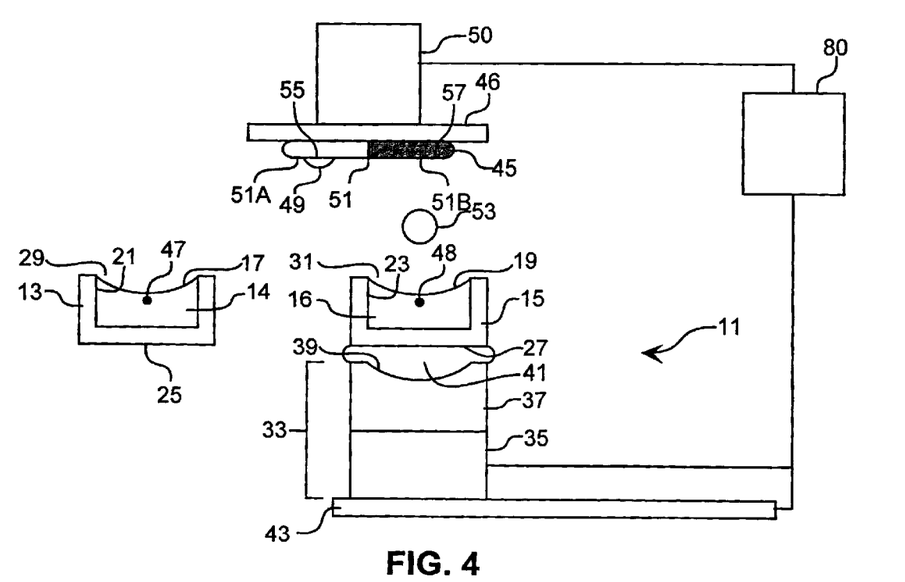
FIG. 4 schematically illustrates in side view the deposition of a second analysis-enhancing fluid on a surface of the tissue sample at a second site selected according to a second surface characteristic.

An exemplary device for acoustically depositing a fluid on a surface of a cellular sample is shown in FIGS. 3 and 4. The device is similar in construction to the acoustic ejection device described in U.S. Patent Application Publication No. 20020037579 to Ellson et al. and in U.S. patent application Ser. No. 10/087372, entitled "Method and System Using Acoustic Ejection for Preparing and Analyzing a Cellular Sample." The device 11 includes two reservoirs, although only one reservoir may be required in some instances. A first reservoir 13 contains the first analysis-enhancing fluid 14, and the second reservoir 15 contains the second analysis enhancing fluid 16. The free surface for fluids 14 and 16 are indicated at 17 and 19, respectively. Typically, fluids 14 and 16 are different when the surface characteristics of regions 51A and 51B are different. In order to prepare the sample surface for mass spectrometric analysis, fluids 14 and 16 each comprise a mass spectrometry matrix material.

The reservoirs are shown in their preferred construction and are substantially identical and acoustically indistinguishable. However, identical construction is not a requirement. In addition, the reservoirs are shown as separate removable components, but they may, if desired, be fixed within a plate or other substrate. For example, the plurality of reservoirs may comprise individual wells in a well plate, optimally (although not necessarily) arranged in an array. Each of the reservoirs 13 and 15 is preferably axially symmetric as shown, having vertical walls 21 and 23 extending upward from circular reservoir bases 25 and 27, and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33, comprised of an acoustic radiation generator 35 for generating acoustic radiation and a focusing means 37 for focusing the acoustic radiation at a focal point within the fluid from which a droplet is to be ejected near the fluid surface. As shown in FIGS. 2 and 3, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet placement and consistency in droplet size and velocity are more easily achieved with a single ejector. However, the invention is not limited to single ejector designs.

Any of a variety of focusing means that include curved surfaces or Fresnel lenses known in the art may be employed in conjunction with the present invention. Such focusing means are described in U.S. Pat. Nos. 4,308,547 to Lovelady et al. and 5,041,849 to Quate et al., as well in as U.S. Ser. Nos. 09/964,212 and 09/669,996. In addition, there are a number of ways to acoustically couple the ejector to each individual reservoir and thus to the fluid therein. Although acoustic coupling can be achieved through direct contact with the fluid contained in the reservoirs, the preferred approach is to acoustically couple the ejector to the reservoirs and reservoir fluids without allowing any portion of the ejector (e.g., the focusing means) to contact any of the fluids to be ejected. To this end, the present invention provides an ejector positioning means for positioning the ejector in controlled and repeatable acoustic coupling with each of the fluids in the reservoirs to eject droplets therefrom without submerging the ejector therein.

To avoid ejector submersion, direct or indirect contact is typically established between the ejector and the external surface of each reservoir. When direct contact is used in order to acoustically couple the ejector to each reservoir, it is preferred that the direct contact be wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs that have a specially formed inverse surface.

Optimally, acoustic coupling is achieved between the ejector and each of the reservoirs through indirect contact, as illustrated in FIGS. 3 and 4. In the figures, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the first reservoir 13 is acoustically coupled to the acoustic focusing means 37 such that an acoustic wave generated by the acoustic radiation generator is directed by the focusing means 37 into the acoustic coupling medium 41, which then transmits the acoustic radiation into reservoir 13.

In operation, reservoirs 13 and 15 of the device are each filled with first and second analysis-enhancing fluids 14 and 16, respectively, as shown in FIG. 3. The combination unit 80 directs the ejector positioning means 43 to position the acoustic ejector 33 below reservoir 13 and to achieve acoustic coupling between the ejector and the reservoir through acoustic coupling medium 41. Cellular sample 45 is positioned by sample positioning means 50 above and in proximity to the first reservoir 13 such that one surface of the tissue, shown in FIG. 1 as the exposed surface 51, faces the reservoir and is substantially parallel to the surface 17 of the fluid 14 therein. In particular, the combination unit 80 may direct the sample positioning means such that site 55 in region 51A is in position to receive a droplet of the first analysis-enhancing fluid 14 from reservoir 13. Once the ejector, the reservoir, and the tissue sample 45 are in proper alignment, the combination unit 80 activates acoustic radiation generator 35 to produce acoustic radiation. The focusing means 37 directs the generated acoustic radiation to a focal point 47 near the fluid surface 17 of the first reservoir. As a result, droplet 49 is ejected from the fluid surface 17 onto the first selected site 55 on surface 51 of the tissue sample. The ejected droplet may be retained on the tissue surface through adsorption and/or other surface effects. Frequently, the analysis-enhancing fluid will contain a volatile liquid component, and much of the liquid component will evaporate shortly after deposition. In some instances, the droplet may be solidified on the tissue surface after contact; in such an embodiment, it may be necessary to maintain the tissue at a low temperature, i.e., a temperature that results in droplet solidification after contact.

Then, as shown in FIG. 4, a sample positioning means 50 repositions the cellular sample 45 on the substrate 46 over reservoir 15 in order to receive a droplet therefrom at the second selected site 57. FIG. 4 also shows that the ejector 33 has been repositioned by the ejector positioning means 43 below reservoir 15 and in acoustically coupled relationship thereto by virtue of acoustic coupling medium 41. Once properly aligned as shown in FIG. 4, the acoustic radiation generator 35 of ejector 33 is activated to produce acoustic radiation that is then directed by focusing means 37 to a focal point 48 within fluid 16 near the fluid surface 19, thereby ejecting droplet 53 onto the cellular sample at the second selected site 57. It should be evident that such operation is illustrative of how the inventive device may be used to eject a plurality of fluids from the same reservoir to the same or different sites, or to eject a plurality of droplets from a plurality of reservoirs onto the same site of the cellular sample surface.

It will be appreciated that various components of the device may require individual control or synchronization to deposit any fluid to a corresponding site on a sample surface. For example, the ejector positioning means may be adapted to eject droplets from each reservoir in a predetermined sequence associated with selected sites on a sample surface. Similarly, the means for positioning the sample with respect to the ejector may be adapted to position the sample surface to receive droplets at appropriate sites. Either or both positioning means (i.e., the ejector positioning means and the sample positioning means) may be constructed from, for example, motors, levers, pulleys, gears, a combination thereof, or other electromechanical or mechanical means known to one of ordinary skill in the art. It is preferable to ensure that there is a correspondence between sample movement, ejector movement, and ejector activation to allow proper fluid deposition. This correspondence may be achieved through the use of a controller unit, e.g., the combination unit 80 as described above.

As alluded to above, the invention is particularly useful in mass spectrometry. The invention is especially suited for use in surface-based mass spectrometric techniques such as MALDI. See Karas et al. (1988), "Laser Desorption Ionization of Proteins with Molecular Masses Exceeding 10,000 Daltons," *Anal. Chem.*, 60:2299–2301. In addition, the invention may be employed in conjunction with a variety of surface-based mass spectrometric techniques other than MALDI. For example, one variant of MALDI, called SELDI, uses affinity capture reagents such as antibodies to collect samples from a complex mixture, which allows in situ purification of the analyte followed by conventional MALDI analysis. The invention exhibits all the advantages in the use of acoustic ejection as described in U.S. patent application Ser. No. 10/087372.

Figure 5:
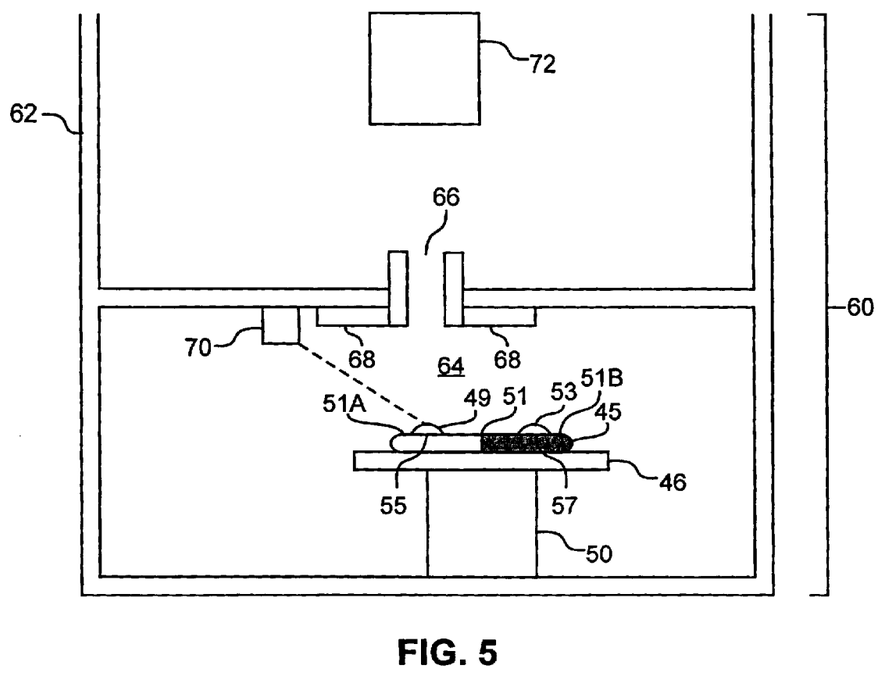
FIG. 5 schematically illustrates in side view the ionization of the sample at the tissue surface sites.

FIG. 5 schematically illustrates an exemplary ionization chamber of a mass spectrometer suitable for use with the invention. The ionization chamber 60 comprises a housing 62 that contains an ionization region 64 and an interface comprising a capillary 66 and an electrode 68 for attracting ions toward the capillary 66. An energy applying means 70 in the form of a laser and a sample positioning means 50 are provided as well. In operation, the substrate 46 is immobilized with respect to the positioning means 50. As shown, the tissue sample 45 has been subjected to conditions effective to allow the analysis-enhancing fluid droplets 49 and 53 to interact with sample surface 51 so as to render the sample surface suitable for analysis at the selected sites 55 and 57, respectively. The electrode 68 is charged, and once the first selected site 55 and the capillary 66 are in proper alignment, the laser 70 is activated. As a result, ionized sample molecules, which have formed at the first selected site 55, are released into ionization region 64. The ions are then drawn toward the electrode 68, enter the capillary 66, and are subsequently analyzed by mass analyzer/detector 72. Examples of such mass analyzers/detectors include multipole detectors, e.g., quadruple detectors, which employ a charged surface that attracts or repels the ionized sample molecule. The identical procedure may be carried out for ionizing sample molecules at the second selected site 57. Additional charged surfaces (not shown) may be placed in the ionization chamber to direct the trajectory of ions.

Thus, it should be evident that the acoustic ejection device illustrated in FIGS. 3 and 4 may share a common registration system with the mass spectrometer illustrated in FIG. 5. This ensures that the sample positioning means for the acoustic ejection device and the mass spectrometer can carry out the identical sample movement system. In turn, laser irradiation will occur at precisely the selected sites. It should be further evident that these procedures may be controlled using commercially available and/or customized software.

Generally, the invention may be practiced using any sample having a nonuniform surface. Thus, the sample may be comprised of organic as well as inorganic materials. Examples of inorganic materials include, but are not limited to metals, ceramics, and semiconductors. When the sample is comprised of an organic material, the material may be living, nonliving, or dead. Nevertheless, the cellular samples are particularly suited for use with the invention. The cellular sample may comprise nearly any type of cell in the present invention. For example, either or both eukaryotic cells and prokaryotic cells may be used. In some instances, cells extracted are obtained from a mammal. Suitable cell types include, for example, blood cells, stem cells, endothelial cells, epithelial cells, bone cells, liver cells, smooth muscle cells, striated muscle cells, cardiac muscle cells, gastrointestinal cells, nerve cells, and cancer cells. Such cells may be taken as a tissue sample. Alternatively, the cellular sample may comprise cells originating from a cultured cell line or other cultured cells.

The cellular sample may be employed in any of a number of forms. Typically, the cellular sample exhibits a substantially planar surface. In addition, cells are typically immobilized on a substrate surface. Thus, a substrate surface may be selected for facile immobilization of a single cell or a plurality of cells. Such surfaces include, for example, a collagen-derivatized surface, dextran, polyacrylamide, nylon, polystyrene, and combinations thereof. In some instances, the surfaces are inherently cytophilic. In other instances, a cytophilic substrate surface is provided as a result of surface modification. In any case, the cells may be immobilized on a substrate surface using conventional techniques known to those skilled in the art and/or as described in U.S. patent application Ser. No. 10/087,372.

The surface characteristic corresponding to desirability for receiving analysis-enhancing fluid is typically a compositional or morphological characteristic. Such characteristics may be optically and/or acoustically detectable. The detectability could may optionally be enhancing by staining or through the use of acoustic contrast enhancement fluids.

Thus, in some embodiments, the inventive system may include a selecting means comprised of a means for imaging of the sample surface so as to map the variations in the surface characteristic and a means for selecting at least one site on the sample surface using the results produced by the imaging means. The imaging means is typically adapted to produce a digital image and may, for example, employ a scanner or a camera. In other instances, an image of the sample surface that maps the variations in the surface characteristic is produced without an imaging means. In either case, the selecting means may select sites for analysis-enhancing fluid deposition when the surface characteristic is above a threshold level and/or when the surface characteristic is within a predetermined range. The selecting means may employ imaging technologies known in the art. A variety of imaging software, firmware, and hardware are commercially available, as well as microscopes and other image magnification devices suitable for providing more detailed resolution of surface inhomogeneities. Optionally, the imaging contrast of the variations in the surface characteristic is increased before the surface is imaged. This may involve, for example, staining or labeling the sample surface such that regions exhibiting the desired surface characteristic is more readily resolved by an imaging means.

In some instances, the sample may exhibit variations in a plurality of surface characteristics, wherein each characteristic corresponds to desirability for receiving a different analysis-enhancing fluid. In such a case, droplets of different analysis-enhancing fluids may be deposited on the sample surface at the corresponding selected sites. In addition, different analysis-enhancing fluids may be deposited on the sample surface at the same site.

The analysis-enhancing fluid may be selected according to the type of analysis desired, preferably to increase yield of useful information during surface analysis. In some instances, the analysis-enhancing fluid comprises a label moiety, such as one or more selected from the group consisting of a fluorescent moiety, a magnetic moiety, and a radioactive moiety. However, it should be noted that label moieties does not have to be employed in conjunction with the analysis-enhancing fluid; such label moieties may be used separately from the use of analysis-enhancing fluid. In addition or in the alternative, the analysis-enhancing fluid may contain biomolecules (such as peptides or nucleotides) and/or cellular matter (such as whole cells and cell extracts). Often, the analysis-enhancing fluid is selected to preferentially interact with selected moieties on a compositionally nonuniform sample surface. For example, if peptidic digestion is desired, then trypsin, pepsin, and other well-known compounds for peptidic digestion may be included in the fluid. Thus, an enzymatic biomolecule such as a protease is provided to enhance breakdown of the corresponding substrate moiety on or near the sample surface.

In addition, the analysis-enhancing fluid may comprise an analysis-enhancing moiety and a carrier fluid. The carrier fluid in such cases may include, for example, combinations of water, acetonitrile, alcohols (such as ethanol), and ketones (such as acetone). Thus, it should be apparent that the invention may involve the ejection of fluids of virtually any type and amount desired, including fluids that do not enhance analysis, although at least one analysis-enhancing fluid is typically used. The fluids may be aqueous and/or nonaqueous. Examples of fluids include, but are not limited to, aqueous fluids (including water per se-and water-solvated ionic and nonionic solutions, organic solvents, and lipidic liquids), suspensions of immiscible fluids, and suspensions or slurries of solids in liquids. Evaporation of the carrier fluid increases the local concentration of the analysis-enhancing moiety to effect interaction between the analysis-enhancing moiety and the substrate surface. Depending on the type of analysis desired, any of a number of different types of interaction might take place between the analysis-enhancing moiety and the sample surface. For example, the analysis-enhancing moiety may be selected to break down or digest the constituents of the sample surface. As another example, the analysis-enhancing moiety may bind with selective moieties on the sample surface, thereby rendering the substrate surface suitable for analysis. Thus, analysis-enhancing fluids may enhance the suitability of a sample to be analyzed by modifying the sample surface.

As discussed above, the invention is particularly suited for mass spectrometric analysis. In order to carry out a surface-based mass spectrometry technique such as a MALDI- or SELDI-type analysis, mass spectrometry matrix material may be deposited onto the sample surface and energy applied to the sample deposited matrix material to release sample molecules from the sample surface for analysis. Typically, the matrix material is a photoabsorbing matrix material, and a photon source such as a laser is used to ionize the sample. Any of a number of photoabsorbing matrix materials known in the art may be employed, and examples of matrix materials for sample analysis include, but are not limited to, 6-aza-2-thiothymine, caffeic acid, sinipinic acid, 2,5-dihydroxybenzoic acid, α-cyano-4-hydroxycinnamic acid, 3-hydroxypicolinic acid, 2-pyrazinecarboxylic acid, and combinations thereof. However, energy may be applied by bombarding the sites with electrons and/or ions as well. Ionization and release of sample molecules may be enhanced through heating, directing focused acoustic energy to, and/or passing an electrical current through at least one site. Once released, the ions may be directed to a mass analyzer in a manner described above or through other known techniques. Further variations relating to mass spectrometric analysis are described in U.S. patent application Ser. No. 10/087,372. It should be noted that mass spectrometric analysis for use with the present invention is not limited to biological materials. For example, the invention may be employed to improve secondary ion mass spectrometry, a technique commonly used in semiconductor industries, as described in U.S. Pat. No. 6,291,820 to Hamza et al.

Means other than mass spectrometry for analyzing the sample may be provided as well. Such analyzing means may include, for example, an optical detector, a radiation detector, and/or a magnetic detector. In some instances, the invention may be used to enhance analysis of inorganic material. One example in which this may be carried out is to selectively deposit a particular etchant on an alloy surface to etch a particular phase of alloy material. As another example, the invention may enhance strain analysis. For instance, U.S. Pat. No. 6,327,030 to Ifju et al. describes a method for measuring strain on a substrate material. The method involves preparing the substrate material for strain measurement by applying a luminescent coating to a substrate material, curing the coating, and illuminating the coating with excitation illumination. Then, characteristics of luminescent light emanating from the coating are measured in order to determine strain on the substrate material. The characteristics of luminescent light emanating from the coating are related to strain on the substrate material due, at least in part, to a relationship between the amount of strain on the substrate material and the morphology of cracks in the coating. The present invention provides a convenient technique to improve such a strain measurement method. Since it is known that some materials exhibit preferential strain proliferation when they possess certain morphological characteristics, e.g., surface scratches and texturing, the coating may be selectively applied only to regions on the substrate that exhibit such morphological characteristics for analysis. In this way, excess coating is not wasted through its application to regions where such characteristics are absent.

Figure 6:
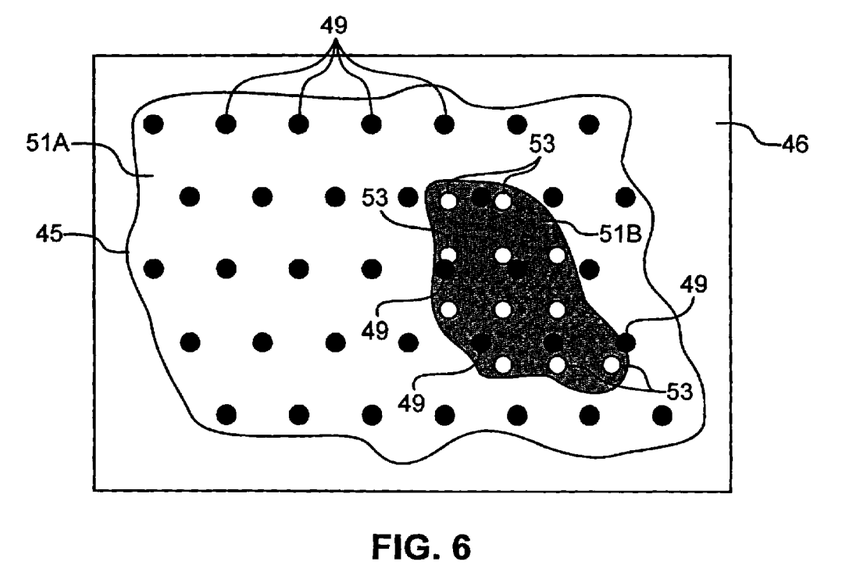
FIG. 6 schematically illustrates in top view a tissue sample exhibiting a nonuniform upper surface having droplets of different analysis-enhancing fluids deposited thereon at different sites. These sites are selected according to specific surface characteristics, and the sites associated with each analysis-enhancing fluid form an array.

It should be noted that the invention may be advantageously used in combination with surface mapping technologies, such as those described in U.S. Pat. No. 5,808,300 to Caprioli and in U.S. patent application Ser. No. 10/087,372. For example, FIG. 6 schematically depicts tissue sample 45 on a substrate 46. The exposed sample surface 51 is nonuniform. As shown, the surface 51 is comprised of a first region 51A circumscribing a second region 51B. The first region 51A may be, for example, comprised of lean tissue and the second region 51B comprised of lipid tissue. In such a situation, it may be desirable to place an analysis-enhancing fluid on only one of the regions. That is, the sites for fluid deposition may be selected according to lipid and/or peptide content at the site. As lipid tissue and lean tissue are typically optically distinguishable from one another, fluid deposition in this instance would involve selecting sites on the surface according to the optical characteristics displayed (i.e., at the sites associated with either lipid or lean tissue).

The invention provides a method that combines the mapping technologies as discussed above with the advantages of enhancement of analysis at a selected region. An example of such combined use is depicted in FIG. 6, wherein droplets of a first analysis-enhancing fluid, indicated at 49, are deposited at a first array of sites on the sample surface 51, and droplets of a second analysis-enhancing fluid, indicated at 53, are deposited at a second array of sites on the sample surface 51. The first fluid enhances peptide analysis while the second fluid enhances lipid analysis. The first fluid is deposited in both regions 51A and 51B, while the second fluid is deposited only within region 51B. Thus, by analyzing the sample at each site having the first fluid deposited thereon, a map of peptide composition of the overall sample surface can be constructed. Similarly, by analyzing the sample at each site having the second fluid deposited thereon, the lipidic region 51B may be selectively analyzed.

Thus, variations of the present invention will be apparent to those of ordinary skill in the art. For example, the inventive system may include a plurality of reservoirs, each containing a different analysis-enhancing fluid. In such a case, the site-selecting means may select sites according to a surface characteristic at the sites that correspond to desirability for receiving at least one of the analysis-enhancing fluids. The selection of the number, size, and type of reservoirs are discussed in detail in U.S. patent application Ser. No. 10/087,372. This patent application also describes the fluid volumes that typify use with the present invention.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

We claim:

1. A method for selectively depositing an analysis-enhancing fluid on a sample surface, comprising:
   (a) providing a sample having a contiguous surface that exhibits variations in a surface characteristic, wherein the surface characteristic corresponds to desirability for receiving an analysis-enhancing fluid;
   (b) selecting a site on the contiguous sample surface according to the surface characteristic at the site; and
   (c) applying focused radiation in a manner effective to eject a droplet of the analysis-enhancing fluid from a reservoir to deposit the droplet on the contiguous sample surface at the selected site.

2. The method of claim 1, wherein the sample is a cellular sample.

3. The method of claim 2, wherein the cellular sample is selected from a tissue sample, a cell culture, a single cell, or a plurality of cells immobilized on a substrate surface.

4. The method of claim 1, wherein the sample surface is substantially planar.

5. The method of claim 1, wherein surface characteristic is a compositional characteristic.

6. The method of claim 5, wherein the compositional characteristic is lipid content.

7. The method of claim 5, wherein the compositional characteristic is peptide content.

8. The method of claim 1, wherein the surface characteristic is a morphological characteristic.

9. The method of claim 1, wherein the surface characteristic is optically detectable.

10. The method of claim 1, wherein the surface characteristic is acoustically detectable.

11. The method of claim 1, wherein the applied focused radiation is acoustic radiation.

12. The method of claim 1, wherein the analysis-enhancing fluid comprises a label moiety.

13. The method of claim 12, wherein the label moiety is selected from the group consisting of a fluorescent moiety, a magnetic moiety, and a radioactive moiety.

14. The method of claim 1, wherein the analysis-enhancing fluid contains a biomolecule.

15. The method of claim 14, wherein the biomolecule is peptidic or nucleotidic.

16. The method of claim 14, wherein the biomolecule is enzymatic.

17. The method of claim 16, wherein the enzymatic biomolecule is a protease.

18. The method of claim 17, wherein the protease is trypsin.

19. The method of claim 1, wherein the analysis-enhancing fluid comprises a mass spectrometry matrix material.

20. The method of claim 19, wherein the mass spectrometry matrix material is a photoabsorbing matrix material.

21. The method of claim 1, wherein step (b) comprises:
(b') imaging the sample surface so as to map the variations in the surface characteristic; and
(b") selecting a site on the sample surface using the results of step (b').

22. The method of claim 21, wherein step (b') is carried out to produce a digital image.

23. The method of claim 21, further comprising, before step (b'), (b°) increasing the imaging contrast of the variations in the surface characteristic.

24. The method of claim 23, wherein step (b°) comprises staining the sample surface.

25. The method of claim 1, wherein a plurality of sites are selected, and a droplet of analysis-enhancing fluid is deposited on each selected site.

26. The method of claim 25, wherein the plurality of sites form a single contiguous region on the sample surface.

27. The method of claim 25, wherein the plurality of sites form a plurality of noncontiguous regions on the sample surface.

28. The method of claim 1, further comprising, after step (c), (d) analyzing the sample at the selected site.

29. The method of claim 28, further comprising, after step (c) and before step (d), (c') applying effective energy to the selected site to release sample molecules from the sample surface for analysis.

30. The method of claim 29, wherein step (d) comprises performing mass spectrometric analysis on the sample molecules.

31. The method of claim 1, wherein the sample exhibits variations in a plurality of surface characteristics, each characteristic corresponds to desirability for receiving a different analysis-enhancing fluid, and steps (b) and (c) are repeated for each surface characteristic such that droplets of different analysis-enhancing fluids are deposited on the sample surface at the corresponding selected sites.

32. The method of claim 31, wherein at least one selected site exhibits surface characteristics such that different analysis-enhancing fluids are deposited on the sample surface at the at least one selected site.

33. A system for selectively depositing an analysis-enhancing fluid on a contiguous surface of a sample, comprising:
a reservoir containing an analysis-enhancing fluid;
an acoustic ejector comprising an acoustic radiation generator for generating acoustic radiation and a focusing means for focusing the acoustic radiation generated;
a means for positioning the acoustic ejector in acoustic coupling relationship to the reservoir;
a means for selecting at least one site on the contiguous sample surface for deposition of analysis-enhancing fluid thereon, wherein the at least one site is selected according to a surface characteristic at the at least one site that corresponds to desirability for receiving the analysis-enhancing fluid;
a means for positioning the sample such that the at least one selected site thereon is positioned in droplet-receiving relationship to the reservoir.

34. The system of claim 33, wherein the selecting means comprises:
a means for imaging of the sample surface so as to map the variations in the surface characteristic; and
a means for selecting at least one site on the sample surface using the results produced by the imaging means.

35. The system of claim 34, wherein the imaging means comprises a scanner.

36. The system of claim 34, wherein the imaging means comprises a camera.

37. The system of claim 34, wherein the imaging means is adapted to produce a digital image.

38. The system of claim 33, wherein the selecting means comprises:
an image of the sample surface that maps the variations in the surface characteristic; and
a means for selecting at least one site on the sample surface using the image of the sample surface.

39. The system of claim 38, wherein the image is a digital image.

40. The system of claim 33, wherein the selecting means selects the at least one site on the sample surface for analysis-enhancing fluid deposition when the surface characteristic is above a threshold level.

41. The system of claim 33, wherein the selecting means selects the at least one site on the sample surface for analysis-enhancing fluid deposition when the surface characteristic is within a predetermined range.

42. The system of claim 33, further comprising a means for analyzing the composition of the sample at the selected site.

43. The system of claim 42, wherein the analyzing means comprises a mass spectrometer.

44. The system of claim 42, wherein the analyzing means comprises a detector selected from the group consisting of optical detectors, fluorescence detectors, radiation detectors, and magnetic detectors.

45. The system of claim 42, further comprising a means for applying energy to the at least one selected site to effect release and ionization of sample molecules from the sample surface for analysis.

46. The system of claim 45, wherein the energy applying means comprises a means for bombarding the at least one selected site with photons.

47. The system of claim 46, wherein the photon bombarding means comprises a laser.

48. The system of claim 33, wherein the sample positioning means is adapted to controllably position the sample such that when a plurality of sites on the sample surface is selected, the selected sites are successively placed in droplet-receiving relationship to the reservoir.

49. A system for selectively depositing a plurality of analysis-enhancing fluids on a contiguous surface of a sample, comprising:
a plurality of reservoirs each containing a different analysis-enhancing fluid;

an acoustic ejector comprising an acoustic radiation generator for generating acoustic radiation and a focusing means for focusing the acoustic radiation generated;

a means for positioning the acoustic ejector in acoustic coupling relationship to each of the reservoirs;

a means for selecting sites on the contiguous surface for analysis-enhancing fluid deposition, wherein the sites are selected according to a surface characteristic at the sites that corresponds to desirability for receiving at least one of the analysis-enhancing fluids; and a means for positioning the sample such that the selected sites on the contiguous surface are placed successively in droplet-receiving relationship to the reservoir containing the analysis-enhancing fluid that corresponds to the surface characteristic at the selected sites.

50. A system for selectively depositing an analysis-enhancing fluid on a contiguous surface of a sample, comprising:

a reservoir containing an analysis-enhancing fluid;

an acoustic ejector comprising an acoustic radiation generator for generating acoustic radiation and a focusing means for focusing the acoustic radiation generated;

a means for positioning the acoustic ejector in acoustic coupling relationship to the reservoir;

a means for positioning the sample such that at least one site on the contiguous sample surface exhibiting a surface characteristic that corresponds to desirability for receiving the analysis-enhancing fluid is placed in droplet-receiving relationship to the reservoir.

51. The system of claim 50, wherein the sample positioning means is adapted to controllably position the sample such that when a plurality of sites on the sample surface exhibits the surface characteristic, the selected sites are successively placed in droplet-receiving relationship to the reservoir.

52. The system of claim 51, wherein the sample positioning means comprises digital information relating the location of the at least one site on the sample surface.

53. A method for selectively depositing an analysis-enhancing fluid on a sample surface, comprising:

(a) providing a sample having a surface that exhibits variations in a surface characteristic, wherein the surface characteristic corresponds to desirability for receiving an analysis-enhancing fluid comprising a mass spectrometry matrix material;

(b) selecting a site on the sample surface according to the surface characteristic at the site; and (c) applying focused radiation in a manner effective to eject a droplet of the analysis-enhancing fluid from a reservoir to deposit the droplet on the sample surface at the selected site.

54. The method of claim 53, wherein the mass spectrometry matrix material is a photoabsorbing matrix material.

55. A system for selectively depositing an analysis-enhancing fluid on a surface of a sample, comprising:

a reservoir containing an analysis-enhancing fluid;

an acoustic ejector comprising an acoustic radiation generator for generating acoustic radiation and a focusing means for focusing the acoustic radiation generated;

a means for positioning the acoustic ejector in acoustic coupling relationship to the reservoir;

a means for selecting at least one site on the sample surface for deposition of analysis-enhancing fluid thereon, wherein the at least one site is selected according to a surface characteristic at the at least one site that corresponds to desirability for receiving the analysis-enhancing fluid when the surface characteristic is (a) above a threshold level and/or (b) is within a predetermined range;

a means for positioning the sample such that the at least one selected site thereon is positioned in droplet-receiving relationship to the reservoir.

* * * * *